United States Patent
Wallström

[11] Patent Number: 5,935,682
[45] Date of Patent: Aug. 10, 1999

[54] FACING SHEET FOR AN ABSORBENT ARTICLE AND METHOD FOR PRODUCING SAME

[75] Inventor: Leif Wallström, Göteborg, Sweden

[73] Assignee: SCA Mölnlycke AB, Göteborg, Sweden

[21] Appl. No.: 08/817,741

[22] PCT Filed: Nov. 7, 1995

[86] PCT No.: PCT/SE95/01316

§ 371 Date: May 6, 1997

§ 102(e) Date: May 6, 1997

[87] PCT Pub. No.: WO96/14814

PCT Pub. Date: May 23, 1996

[30] Foreign Application Priority Data

Nov. 9, 1994 [SE] Sweden .................... 9403850

[51] Int. Cl.⁶ .............. B32B 3/24; A61F 13/46; B26F 1/24
[52] U.S. Cl. .......... 428/138; 428/137; 428/156; 428/913; 604/378; 604/383; 493/365; 83/866; 83/867; 83/678; 83/674
[58] Field of Search .................... 428/137, 156, 428/138, 913; 493/365; 83/866, 867, 678, 674; 604/378, 383

[56] References Cited

U.S. PATENT DOCUMENTS

| | | | |
|---|---|---|---|
| 1,589,569 | 6/1926 | Schumacher | 83/117 |
| 3,577,507 | 5/1971 | Corbett | 83/867 |
| 3,827,321 | 8/1974 | Bley | 83/117 |
| 4,143,568 | 3/1979 | Cogswell | 83/116 |
| 4,184,619 | 1/1980 | Stewart et al. | 225/94 |
| 4,341,217 | 7/1982 | Ferguson et al. | 128/290 W |
| 4,591,523 | 5/1986 | Thompson | 428/131 |
| 4,626,254 | 12/1986 | Widlund et al. | 604/383 |
| 4,780,352 | 10/1988 | Palumbo | 428/138 |
| 4,781,962 | 11/1988 | Zamarripa et al. | 428/138 |
| 4,908,026 | 3/1990 | Sukiennik et al. | 604/378 |
| 5,216,962 | 6/1993 | Parigi et al. | 83/344 |
| 5,328,450 | 7/1994 | Smith et al. | 602/59 |
| 5,614,283 | 3/1997 | Potnis et al. | 428/131 |
| 5,635,276 | 6/1997 | Biagioli et al. | 428/132 |
| 5,674,211 | 10/1997 | Ekdahl | 604/383 |

FOREIGN PATENT DOCUMENTS

| | | |
|---|---|---|
| 0 214 608 A2 | 3/1987 | European Pat. Off. . |
| 0 235 309 A1 | 9/1987 | European Pat. Off. . |
| 2 235 878 | 3/1991 | United Kingdom . |

Primary Examiner—William P. Watkins, III
Attorney, Agent, or Firm—Burns, Doane, Swecker & Mathis, L.L.P.

[57] ABSTRACT

A facing sheet (10) for absorbent articles is disclosed in the form of a laminate made up of at least a first layer (12) and a second layer (14). The first layer is intended to face a wearer when the absorbent article is in use and presents a plurality of through holes (16) delimited by an upper perimeter (18) and a lower perimeter (20) to thereby permit liquid to migrate through to the second layer (14). The second layer presents first depressions (22) which are arranged such that the lower perimeter (20) of each hole in the first layer (12) is aligned with an associated depression in the second layer (14). The invention further relates to a method which may be used to produce such a facing sheet.

12 Claims, 2 Drawing Sheets

FACING SHEET FOR AN ABSORBENT ARTICLE AND METHOD FOR PRODUCING SAME

TECHNICAL FIELD

The present invention relates to a facing sheet for an absorbent article according to the preamble of claim 1 and claim 7, and a method of producing a facing sheet according to the preamble of claim 8 and claim 9.

BACKGROUND OF THE INVENTION

Absorbent articles such as sanitary napkins, disposable diapers and incontinence pads are generally made up of an absorbent core sandwiched between a liquid permeable facing sheet and a liquid impermeable backing sheet. The facing sheet contacts the wearer and is either naturally permeable or is apertured to allow discharged bodily fluids to pass through the facing sheet to be thereafter retained in the absorbent core.

With absorbent articles of this nature, it is of particular importance that the facing sheet imparts the impression of dryness, even when the article has been worn for an extended period of time. In addition, the facing sheet must feel comfortable when contacting the skin of the wearer.

Whilst the facing sheet must be permeable to allow fluid to pass through to the absorbent core, the facing sheet should not suffer from rewetting when the absorbent article is subjected to compressive forces which may arise as a result of movement of the wearer. On the other hand, it is important that the apertures in the facing sheet remain open even when the absorbent article is compressed, otherwise discharged fluid will collect on the surface of the facing sheet.

Various facing sheets are documented in patent literature. By way of example, an apertured plastics facing sheet is disclosed in U.S. Pat. No. 4,626,254 in which the apertures are located in depressions arranged in the upper layer of the facing sheet, with the apertures being formed in vertical walls of the depressions. Such a facing sheet is however relatively complicated to manufacture since high precision is required to form the apertures.

A facing sheet is described in EP-A-0 235 309 which comprises non-woven fabric having two layers of different fibre compositions. The layer of the fabric which faces the wearer is apertured. Such a facing sheet is made by forming the first layer by subjecting a fibrous web to a high velocity water jet treatment on a support carrying aperture formation elements, forming the second layer by subjecting a fibrous web to either water treatment or heat fusion treatment, and simultaneously combining the first layer with the second layer by either of these treatments. A disadvantage with such a process is that the process is utilizable on a restricted number of different materials only.

GB-A-2 235 878 describes a facing sheet made up of an apertured hydrophobic resin film and a liquid retentive structure body having a hydrophillic surface and a three-dimensional skeleton structure. The skeleton structure comprises a plurality of randomly distributed pores which communicate with the apertures in the resin film to allegedly allow the rapid introduction of a liquid into an absorbent. The apertures in the resin film may be formed by blow moulding and generally have a diameter lying between 1 and 5 mm. Due to the random distribution of the pores in the skeleton structure, it is difficult to accurately predict the rate of liquid take up of such a facing sheet.

An absorbent article is disclosed in U.S. Pat. No. 4,908,026 having a perforated liquid pervious bodyside liner and a flow zone control layer underlying the perforated region of the bodyside liner. During the perforating process, loose elements of the bodyside liner become entangled with hairy meltblown fibres of the flow zone control layer. It is stated that the loose elements are believed to aid in the transfer of liquid through the flow zone control layer.

U.S. Pat. No. 4,341,217 describes an absorbent article having a perforated outer wrap of liquid impermeable material provided with a multiplicity of protuberances projecting toward an absorbent core. By selecting a particular combination of size and depth of the protuberances, it is asserted that the outer wrap can be made to function both as a topsheet portion and as a backsheet portion.

EP-A-0 214 608 describes an apertured facing sheet comprising a non-woven web network of essentially unbroken thermoplastic fibres. Each aperture is formed by a heated pin which penetrates the nonwoven fabric and separates the fibres thereof, with heat from the pin causing the separated fibres to consolidate and set to prevent subsequent closing of the hole. A disadvantage with such a facing sheet is that the equipment necessary for its manufacture requires very close tolerances since each pin tip has to pass into a corresponding hole with perfect clearance. Again, such apparatus is suitable only for making relatively large diameter apertures.

A further process for forming an apertured plastics facing sheet is to heat a plastic film with hot air as the film passes around an apertured roll. By applying a vacuum within the roll, portions of the plastic film are drawn into the apertures of the roll and burst to thereby create corresponding apertures in the facing sheet. Due however to the application of heat, the properties of the sheet are altered. In addition, the lower periphery of each of the thus burst apertures is uneven and the apertures themselves have a tendency to close when the sheet is subjected in use to compressive forces.

SUMMARY OF THE INVENTION

It is therefore an object of the present invention to provide a facing sheet having an apertured first layer which fulfils the requirements of comfort and cleanliness and which is easier to manufacture than previous facing sheets.

This object is achieved by a facing sheet according to claim 1 and a facing sheet according to claim 7.

It is a further object of the present invention to provide a method of producing a facing sheet for use in an absorbent article in which the hole size and dispersion can be accurately controlled to provide exact flow characteristics of a liquid through the facing sheet.

This object is achieved in accordance with the present invention by a method according to claim 8 and a method according to claim 9.

Preferred embodiments of the facing sheet and method are detailed in the respective dependent claims.

The provision of depressions in the second layer of the facing sheet according to the invention implies that the surface area of material of the second layer which is exposed to the liquid as it flows through the holes in the first layer can be selected depending on the depth of the depressions. In addition, the greater the depth of depression, the shorter the flow path through the second layer to the underlying absorbent core. In this manner, the flow characteristics of the liquid through the facing sheet to the underlying absorbent core can be accurately controlled. That material of the facing sheet is removed by a milling process implies that very accurate control of the depth of material removal can be attained.

BRIEF DESCRIPTION OF THE DRAWINGS

The invention will be described in the following in greater detail by way of example only and with reference to the attached drawings, in which.

DETAILED DESCRIPTION OF PREFERRED EMBODIMENTS

Figure 1:
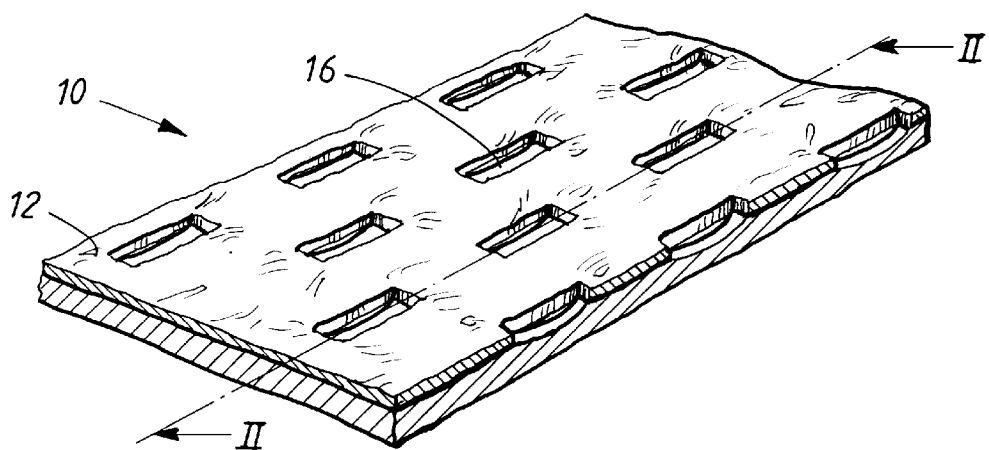
FIG. 1 is a schematic perspective view of a portion of facing sheet according to the invention.

In the drawings, reference numeral 10 generally denotes a facing sheet according to the present invention. The facing sheet is intended to be used in absorbent articles such as sanitary towels, diapers or bandages which, in addition to a facing sheet, further comprise a liquid impermeable backing sheet and an absorbent core located therebetween.

Figure 2:
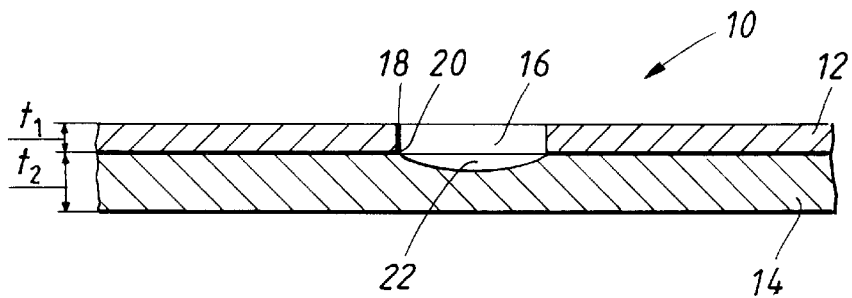
FIG. 2 is a schematic sectional view along line II—II of FIG. 1, though on a larger scale.

The facing sheet 10 illustrated in FIGS. 1 and 2 comprises a laminate made up of a first layer 12 and a second layer 14. Preferably, the layers making up the laminate are substantially coextensive to thereby form a unitary, substantially homogeneous facing sheet. When used in conjunction with an absorbent article, the first layer 12 is uppermost, i.e. the first layer 12 is intended to face the wearer of the absorbent article. As is common in the art, the first layer is provided with a plurality of through holes 16. As is most clearly shown in FIG. 2, each hole 16 is delimited by an upper perimeter 18 and a lower perimeter 20. In this manner, liquid discharged onto the first layer 12 can migrate through the holes 16 to the second layer 14. Preferably, the first layer 12 has a thickness between 5 and 30 $\mu$m and the second layer has a thickness between 10 and 70 $\mu$m.

In accordance with one aspect of the present invention, the second layer 14 presents first depressions 22 which are arranged such that the lower perimeter 20 of each hole 16 in the first layer 12 is aligned with an associated depression 22 in the second layer 14. By selecting a suitable size of through hole 16 and depth of depression 22, the rate of flow of discharged liquid through the facing sheet 10 can be accurately controlled. By way of example, a through hole 16 may have a cross-sectional area of between 1.0 and 25 mm$^2$, whilst a suitable depth for a depression 22 may lie between 5 and 50 $\mu$m.

In order to hinder discharged bodily fluids from remaining on the surface of the facing sheet 10, the first layer may comprise a generally hydrophobic material and the second layer advantageously comprises a generally hydrophillic material. As will be apparent from the subsequent description of the method in accordance with the invention for producing a facing sheet, since the method can be practised on a wide variety of materials, the facing sheet of the present invention may include a first layer of film, nonwoven or woven fibres. Suitable materials include polyethylene, polypropylene, polyester, acrylic, nylon, PVC, hydrophobic cotton fibres or similar. Typically, the first layer consists of a polyethylene-polypropylene film. The second layer may include any of these materials or rayon fibres, a foam-plastic, polyester or cellulose fibres.

Figure 3:
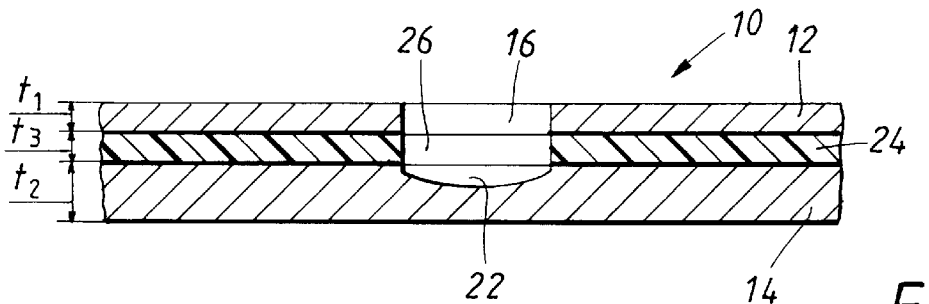
FIGS. 3 and 4 correspond to FIG. 2, though illustrate different embodiments of the facing sheet according to the invention.

A second embodiment of the facing sheet in accordance with the present invention is illustrated in FIG. 3. In common with the facing sheet of FIGS. 1 and 2, the facing sheet in FIG. 3 comprises a first layer 12 with through holes 16 and a second layer 14 with first depressions 22 aligned with the through holes in the manner as described above. In contrast to the previously described facing sheet, the facing sheet of FIG. 3 is provided with a third layer 24 located between the first and second layer. This third layer advantageously comprises a plastics film which serves to inhibit rewetting of the first layer. In order to permit liquid to migrate from the first layer 12 to the second layer 14, the third layer 24 exhibits through holes 26 aligned with the through holes 16 of the first layer.

Figure 4:
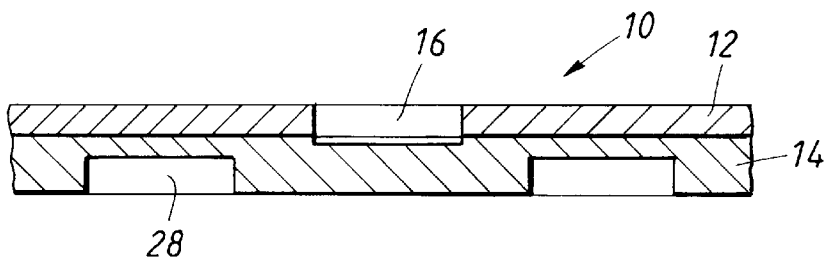

A further embodiment of the facing sheet in accordance with the present invention is illustrated in FIG. 4. In this embodiment, the second layer 14 presents second depressions 28 extending into the second layer to a predetermined depth measured from the surface of the second layer remote from the first layer. Advantageously, these second depressions lie offset relative to the first depressions 22. In this manner, the length of the liquid flow path, i.e. the amount of material in the second layer through which discharged liquid must flow before reaching the underlying absorbent core, can be shortened whilst still maintaining adequate strength in the facing sheet.

The above described embodiments of the facing sheet according to the present invention may advantageously be produced using the method described below which forms another aspect of the present invention.

Figure 5:
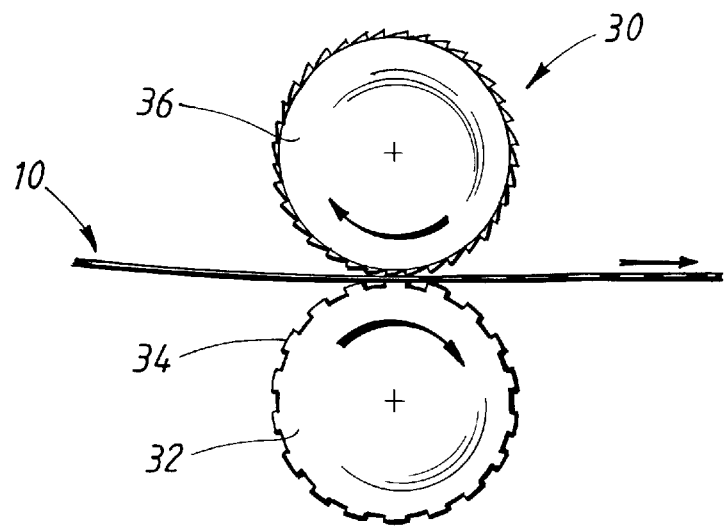
FIG. 5 is a schematic representation of one stage in the manufacturing process for making a facing sheet, whilst
Figure 6:
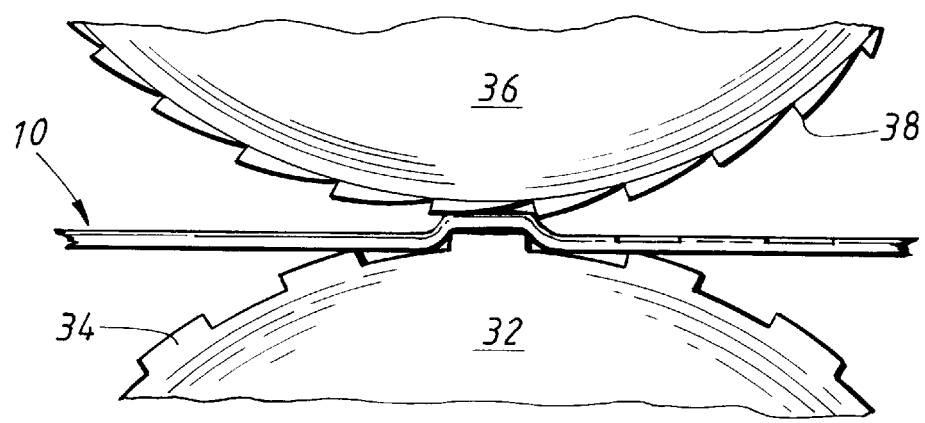
FIG. 6 shows on an enlarged scale a portion of the equipment illustrated in FIG. 5.

Thus, the present invention provides a method for producing a facing sheet for absorbent articles in which the sheet has a first major surface and a second major surface and comprises at least two material layers. With particular reference to FIGS. 5 and 6, the method involves passing the facing sheet 10 between a first set of rollers 30 comprising a pattern roller 32 having a plurality of projections 34 and a milling cutter 36 having cutting edges 38 so that a portion of the material layer is removed to a predetermined depth from the first major surface.

As is most clearly apparent from FIG. 6, the projections 34 on the pattern roller 32 cause the facing sheet to be lifted in a region in which it is desired to remove material. Depending on the ratio between the thickness of the facing sheet and the clearance between the upper surface of the projection 34 and the cutting edge 38, a predetermined depth of material can be removed from the facing sheet. The cross sectional area of each hole which is so produced is dependent on the cross sectional area of the projection 34, assuming that the cutting edge 38 extends across the entire width of the projection.

It will be readily apparent that by providing pattern rollers having different sizes and distribution of projections, apertured facing sheets can be produced having through holes of particular size and selected position.

Although the above method may be utilized on a facing sheet consisting of just one material layer, the method is eminently suitable for producing the facing sheet as illustrated in FIGS. 1 to 4 in which a plurality of material layers is present.

Thus, and with reference to FIG. 2, when the facing sheet comprises a laminate made up of a first layer 12 having a first thickness $t_1$ and a second layer 14 having a second thickness $t_2$, the predetermined depth of the material removed from the facing sheet is selected to be greater than the first thickness $t_1$ though less than the sum of the first and second thickness.

Similarly, and with reference to FIG. 3, when the facing sheet includes a third layer 24 having a third thickness $t_3$ located between the first and second layer, the predetermined depth of material removed from the facing sheet is chosen to exceed the sum of the first and third thickness, though is less than the sum of the first, second and third thickness.

The embodiment of the invention illustrated in FIG. 4 may be obtained by firstly creating holes and depressions to a predetermined depth from the first major surface of the facing sheet as described above, and then subsequently passing the facing sheet through a second set of rollers comprising a pattern roller having a plurality of projections and a milling cutter having cutting edges so that a portion of said material layer is removed to a predetermined depth from the second major surface.

Naturally, it is to be understood that the present invention is not restricted to the embodiments described above and shown in the drawings, but may instead be varied within the scope of the appended claims. For example, the number of material layers making up the facing sheet may be more than three.

I claim:

1. A facing sheet for absorbent articles comprising a laminate made up of at least a first layer and a second layer, said first and second layers being substantially coextensive, said first layer being intended to face a wearer when the absorbent article is in use and comprising a plurality of through holes delimited by an upper perimeter and a lower perimeter to thereby permit liquid to migrate through to the second layer, said second layer presents first depressions which are arranged such that the lower perimeter of each hole in the first layer is axially aligned with an associated depression in the second layer, with each hole and associated depression being concentric, and said second layer presents second depressions extending into said second layer to a predetermined depth measured from the surface of the second layer remote from said first layer.

2. The facing sheet according to claim 1, wherein said first layer comprises a generally hydrophobic material and in that said second layer comprises a generally hydrophillic material.

3. The facing sheet according to claim 1, a third layer is located between said first and second layer, said third layer comprising an apertured plastics film, the apertures of which are concentric with the through holes of said first layer.

4. The facing sheet according to claim 1, wherein said second depressions lie offset relative to said first depressions.

5. The facing sheet according to claim 1, wherein said first layer has a thickness between 5 and 30 µm and in that said second layer has a thickness between 10 and 70 µm.

6. A facing sheet for absorbent articles comprising a laminate made up of at least a first layer and a second layer, said first and second layers being substantially coextensive, said first layer being intended to face a wearer when the absorbent article is in use and comprising a plurality of through holes delimited by an upper perimeter and a lower perimeter to thereby permit liquid to migrate through to the second layer, said second layer presents first depressions formed by the removal of material from said second layer, which depressions are arranged such that the lower perimeter of each hole in the first layer is axially aligned with an associated depression in the second layer, and said second layer presents second depressions extending into said second layer to a predetermined depth measured from the surface of the second layer remote from said first layer.

7. A method for producing a facing sheet for absorbent articles, said sheet comprising a laminate made up of a first layer having a first thickness and a second layer having a second thickness, said first layer forming a first major surface of said sheet and said second layer forming a second major surface of said sheet, the method comprising the steps of passing the facing sheet between a first set of rollers comprising a pattern roller having a plurality of projections and a milling cutter having cutting edges so that a portion of said material layer is removed to a predetermined depth from said first major surface, said predetermined depth being greater than said first thickness though less than the sum of said first and said second thicknesses.

8. A method for producing a facing sheet for absorbent articles, said sheet comprising a laminate made up of a first layer having a first thickness, a second layer having a second thickness and a third layer having a third thickness, wherein said third layer is located between said first and second layer, said first layer forming a first major surface of said sheet and said second layer forming a second major surface of said sheet, the method comprising the steps of passing the facing sheet between a first set of rollers comprising a pattern roller having a plurality of projections and a milling cutter having cutting edges so that a portion of said material layer is removed to a predetermined depth from said first major surface, said predetermined depth exceeding the sum of said first and third thickness, though being less than the sum of the first, second and third thicknesses.

9. The method according to claim 7, further comprising subsequently passing said facing sheet through a second set of rollers comprising a pattern roller having a plurality of projections and a milling cutter having cutting edges so that a portion of said material layer is removed to a predetermined depth from said second major surface.

10. The method according to claim 8, further comprising subsequently passing said facing sheet through a second set of rollers comprising a pattern roller having a plurality of projections and a milling cutter having cutting edges so that a portion of said material layer is removed to a predetermined depth from said second major surface.

11. The method according to claim 7, wherein the milling cutter removes material from the first and second layers.

12. The method according to claim 8, wherein the milling cutter removes material from the first and second layers.

* * * * *